(12) United States Patent
Hayakawa et al.

(10) Patent No.: US 8,865,432 B2
(45) Date of Patent: Oct. 21, 2014

(54) METHOD FOR PREPARING CELLULOSE DERIVATIVES HAVING SOLUBILITY IMPROVED

(75) Inventors: Kazuhisa Hayakawa, Joetsu (JP); Yuichi Nishiyama, Joetsu (JP); Tatsuo Endo, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 1835 days.

(21) Appl. No.: 11/569,360

(22) PCT Filed: Aug. 22, 2005

(86) PCT No.: PCT/JP2005/015191
§ 371 (c)(1),
(2), (4) Date: Nov. 19, 2006

(87) PCT Pub. No.: WO2007/023513
PCT Pub. Date: Mar. 1, 2007

(65) Prior Publication Data
US 2009/0176277 A1 Jul. 9, 2009

(51) Int. Cl.
*C12P 19/00* (2006.01)
*C12P 19/04* (2006.01)
*C08B 15/00* (2006.01)
*C12P 19/14* (2006.01)

(52) U.S. Cl.
CPC ............. *C12P 19/14* (2013.01); *C12P 19/04* (2013.01); *C08B 15/00* (2013.01)
USPC ............................................. 435/72; 536/124

(58) Field of Classification Search
CPC .......... C08B 15/00; C12P 19/14; C12P 19/04
USPC ............................................. 435/72; 536/124
See application file for complete search history.

(56) References Cited

U.S. PATENT DOCUMENTS

| | | | | |
|---|---|---|---|---|
| 4,061,859 | A | * | 12/1977 | Cheng ............................... 536/88 |
| 5,354,424 | A | | 10/1994 | Rha et al. |
| 5,525,368 | A | | 6/1996 | Rha et al. |
| 5,543,162 | A | | 8/1996 | Timonen et al. |
| 5,569,483 | A | | 10/1996 | Timonen et al. |
| 6,261,218 | B1 | * | 7/2001 | Schulz ............................... 536/84 |
| 6,306,333 | B1 | * | 10/2001 | Rosenberg et al. ........ 264/297.1 |
| 6,366,755 | B1 | | 4/2002 | Takashima |
| 2001/0007028 | A1 | | 7/2001 | Schulz |
| 2001/0020090 | A1 | | 9/2001 | Becker et al. |
| 2002/0168407 | A1 | | 11/2002 | Koch et al. |
| 2004/0242862 | A1 | | 12/2004 | Hammes |

FOREIGN PATENT DOCUMENTS

| | | | |
|---|---|---|---|
| AU | 631 842 | B2 | 12/1992 |
| EP | 0 210 917 | A2 | 2/1987 |
| EP | 0 382 577 | A | 8/1990 |
| EP | 0 497 985 | A | 8/1992 |
| EP | 0 676 415 | A | 10/1995 |
| GB | 2 281 073 | A | 2/1995 |
| JP | 1111770 | A | 4/1989 |
| JP | 2245001 | A | 9/1990 |
| JP | 2245002 | A | 9/1990 |
| JP | 5339301 | A | 12/1993 |
| JP | 6225101 | A | 8/1994 |
| JP | 08-027201 | | 1/1996 |
| JP | 8146501 | A | 6/1996 |
| JP | 10237427 | A * | 9/1998 |
| JP | 2001 288201 | A | 10/2001 |
| JP | 2002 531594 | W | 9/2002 |
| JP | 2004 526845 | W | 9/2004 |
| JP | 2005 239845 | A | 9/2005 |
| WO | WO 00/32637 | A | 6/2000 |
| WO | WO 0059947 | A1 * | 10/2000 |
| WO | WO 01/18062 | A | 3/2001 |
| WO | WO 02/081524 | A | 10/2002 |
| WO | WO 03/018637 | A1 | 3/2003 |
| WO | WO 2004/007559 | A | 1/2004 |
| WO | WO 2005118649 | A1 * | 12/2005 |

OTHER PUBLICATIONS

Rowlett, R. "How many? A Dictionary of Units of Measurement" web site: unc.edu/~rowlett/units/discC.html; 22 pages, downloaded on Apr. 5, 2010.*
Derwent abstract for JP 10237427; downloaded from Derwent on Aug. 12, 2011.*
Kotz et al. "Chemistry and Chemical Reactivity" Second eidtion. (1991) (Saunders College Publishing: Ft. Worth, TX) pp. 562-570.*
International Search Report dated Oct. 4, 2005.
Office Action for European Application No. 05 772 486.6 dated Feb. 21, 2012.
Japanese Office Action for Japanese Application No. 2004-050654, dated Jul. 28, 2009.
European Search Report for EP Application No. 05 77 2486.6, dated Jan. 14, 2009.

* cited by examiner

Primary Examiner — Susan Hanley
(74) Attorney, Agent, or Firm — Alston & Bird LLP

(57) ABSTRACT

Provided is a method for preparing a cellulose derivative having solubility improved and therefore having less undissolved floating portions when the derivative is added into water. More specifically, provided is a method for preparing a cellulose derivative, comprising a step of depolymerizing a cellulose derivative to produce a depolymerized cellulose derivative having a viscosity at 20° C. in a 2% by weight aqueous solution of the depolymerized cellulose derivative reduced by at least 10% compared with that of the cellulose derivative before the depolymerization so that the number of undissolved floating portions in the aqueous solution of the depolymerized cellulose derivative is decreased compared with that of the cellulose derivative before the depolymerization. Depolymerization is effected preferably by an acid, alkali or enzyme.

4 Claims, No Drawings

METHOD FOR PREPARING CELLULOSE DERIVATIVES HAVING SOLUBILITY IMPROVED

TECHNICAL FIELD

The present invention relates to cellulose derivatives suited for use as a binder for molding or forming ceramics into plates, rods, pipes and honeycombs; a thickener or a flowability controlling agent to be added to cement mortars or concrete materials before hardening; a starch to be used when a chemical is applied to paper in a preparation of special paper; a coating agent for paper, seeds, plants and industrial materials; a shape-forming agent, sustained release agent or coating agent for pharmaceutical tablets or granules; a base material for hard or soft capsules; a shape-forming binder for processed food, health food, feedstuff or bait; a suspension stabilizer for suspension polymers such as polyvinyl chloride and polyvinylidene chloride; a suspension stabilizer for cosmetics or food; a thickener for shampoos, rinses or cosmetics; and a bond, a thickener, a flowability controller, a covering agent, or a package or packing film-forming agent for various industrial materials, personal consumption materials and household goods.

BACKGROUND ART

Cellulose which is a main component of pulp prepared by purification of wood or cotton linter cannot be molecularly dispersed even if it is dispersed in water owing to hydrogen bonding between hydroxyl groups existing in its molecule. This is presumed to occur because cellulose is a high molecule and its crystalline portion formed by the hydrogen bonding disturbs hydration, whereby the cellulose is insoluble in water. The molecular dispersion in water is improved by derivatizing the hydroxyl group portion of the cellulose derivative by an ester or ether bond to break the hydrogen bonding.

Cellulose is soluble only in a special solvent such as a copper ammonia solution, carbon disulfide with caustic soda, or dimethylsulfoxide/paraformaldehyde. When the cellulose is derivatized, addition of a derivatization reagent to the cellulose in the molecularly dispersed state after dissolving in a solvent is not commonly done in the industry because of difficulty in recovery or reuse of the solvent. Particularly when a cellulose derivative having water solubility is prepared, cellulose in the solid form is dispersed in an alkali solution for activation of the reaction or is impregnated in an alkali, and is then brought into contact with a reaction reagent to derivatize the cellulose. The reaction reagent does not freely cause reaction with the three hydroxyl groups existing around pyranose rings which are repeating structures of cellulose. For example, all of the hydroxyl groups around chained pyranose rings have no reaction, or only one of these hydroxyl groups has reaction. Consequently, portions at which an intramolecular hydrogen bond cannot be broken may exist at intervals of several tens or several hundreds of μm.

When a cellulose derivative having a portion in which the reaction has not progressed sufficiently is dissolved in water, even if the reaction reagent clings to the cellulose derivative in form of replacement or addition, a portion in which a hydrogen bond between hydroxyl groups is broken is dissolved in water, while a portion, in which the reaction has not progressed sufficiently and an amount of replacement of or addition to the hydroxyl group of the cellulose by the reaction reagent is low, is insoluble and floating in water.

Cellulose derivatives are used for various purposes. When they are used for film formation, an undissolved floating portion sometimes impairs the quality of the resulting film. For example, conventional extruded ceramic products are manufactured as follows. Main ceramic materials are mixed, calcined and ground to produce a nonplastic ceramics powder. Added thereto are a cellulose derivative as a binder for imparting it with plasticity, water for dissolving the binder therein, an optional plasticizer and an optional lubricant. The resulting mixture is kneaded (mixing while tearing into pieces using a roll mill, a continuous kneader or the like) to produce a argil. Alternately, the binder dissolved in water is kneaded with the ceramic powder sufficiently to produce an argil. The argil is extruded and then calcined to produce a green body. Particularly when a green body such as a ceramic sheet for electronic materials which need high quality is prepared, a water-soluble cellulose ether such as methoxy-containing methyl cellulose has been used widely as the binder to enhance water retention and shape retention of the argil and to impart it with plasticity suited for extrusion even by the addition of a small amount.

In order to obtain cellulose ether having a desired polymerization degree, raw material cellulose having a polymerization degree within a predetermined range is selected and subjected to etherification reaction. Alternatively, cellulose (pulp) having a proper polymerization degree is selected and dipped in an alkali solution to yield an alkali cellulose. The resulting alkali cellulose is allowed to stand (be aged) in the air under appropriate conditions (temperature, time and the like) and then subjected to etherification reaction. Particularly, cellulose ether to be used as a material for extrusion of ceramics preferably has a polymerization degree corresponding to the viscosity at 20° C. of from 25 to 200,000 mPa·s in a 2% by weight aqueous solution. When it has a polymerization degree falling within this range, it can be extruded easily because of low stickiness during extrusion and the extruded product does not crack during drying.

Such cellulose ether is obtained by ether substitution of natural cellulose, which is essentially insoluble in water, in order to give it water solubility. The substitution reaction is a solid/liquid reaction between cellulose and an etherifying agent as described above so that the reaction tends to be heterogeneous in the industrial-scale production and a low-substituted portion is not easily soluble in water. When such cellulose ether is employed for extrusion of ceramics, an undissolved portion of the cellulose ether remains in the extruded product and the subsequent calcinations generates pores of about several μm.

Existence of such pores may be an obstacle for the preparation of an IC substrate in which conductive and insulator layers having thickness of about 10 to 20 μm are printed on a sintered substrate. These pores also deteriorate withstanding voltage properties of ceramics sintered body for a dielectric such as a capacitor. According to Japanese Patent Provisional Publication No. 01-111770, there is a strong demand for the development of ceramic materials having no such defects.

In addition, cellulose ether having a low polymerization degree or cellulose ester formed by esterification of the cellulose ether and made enteric such as hydroxypropylmethyl cellulose acetate succinate, hydroxypropylmethyl cellulose phthalate or cellulose acetate phthalate is dissolved in a solution of alkali such as ammonia and the resulting solution is spray-coated onto tablets or granules containing a drug and dried. When an undissolved portion exists, a spray gun is clogged therewith or a coated part contains defects, leading to problems that contrary to the intended purpose of the coating, bitterness of the drug is tasted or the drug is released in the stomach from the defective portion because a function of masking the bitterness of the drug or releasing the drug not in the stomach but in the intestine is not fulfilled.

DISCLOSURE OF THE INVENTION

An object of the present invention is to provide a method for preparing a cellulose derivative having water solubility improved in order to prevent disturbance by undissolved portions (the undissolved portions contains fibrous materials and/or entanglement thereof) so that when it is dissolved in water, the number of undissolved floating portions in water is very low.

It has been found that undissolved portions of a water-soluble cellulose derivative decrease by depolymerizing the derivative with an acid or alkali, or with an enzyme to obtain the depolymerized cellulose derivative having a viscosity at 20° C. in a 2% by weight aqueous solution of the depolymerized derivative reduced by at least 10%. Thus, the present invention has completed. In general, hydrolysis or enzymatic decomposition of cellulose with an acid or alkali hardly occurs at a portion where etherification or esterification has progressed. Although depolymerization occurs by the decomposition of an ether bond between pyranose rings, the ether bond between pyranose rings at which derivatization such as etherification or esterification has progressed is not broken easily. A bond between pyranose rings which have not been subjected to substitution or addition so that derivatization such as etherification or esterification has not progressed can be broken more easily. When one or two pyranose rings which have not been derivatized are bonded, the resulting cellulose derivative has a structure of monosaccharide or disaccharide, and formation of a hydrogen bond bringing a specific structure facilitates hydration with water so that the resulting cellulose derivative becomes soluble in water. In other words, as a result of depolymerization, the depolmerized cellulose derivative becomes rich in chained portions of pyranose rings which have been subjected to substitution or addition to the extent that it facilitates dissolution in water so that the depolymerized cellulose ether have many portions which can facilitate dissolution in water. In this manner, undissolved portions can be reduced.

In the present invention, there is thus provided a method for preparing a cellulose derivative, comprising a step of depolymerizing a cellulose derivative to produce a depolymerized cellulose derivative having a viscosity at 20° C. in a 2% by weight aqueous solution of the depolymerized cellulose derivative reduced by at least 10% compared with that before the depolymerization so that the number of undissolved floating portions in the aqueous solution of the depolymerized cellulose derivative is decreased compared with that before the depolymerization. The depolymerization may be effected preferably by an acid, an alkali or an enzyme. The viscosity is measured in accordance with the Japanese Pharmacopoeia.

BEST MODE FOR CARRYING OUT THE INVENTION

There are examples where cellulose ether employed as a binder for ceramics is adjusted to have an appropriate viscosity by adding an aqueous alkali solution to a cellulose raw material, and depolymerizing (or also referred to as aging) the cellulose with alkali in the presence of oxygen to reduce its polymerization degree. It has been found that any of the above-described problems can be overcome by using not cellulose having a polymerization degree adjusted to fall within a desired range prior to etherification but cellulose ether having a polymerization degree reduced in a certain degree by depolymerization with an acid, alkali or enzyme after etherification, leading to the completion of the invention.

The cellulose derivative to be used in the present invention is cellulose having water solubility improved by the introduction of a substituent therein. Specific examples may include water-soluble cellulose ethers such as carboxymethyl cellulose, methyl cellulose, hydroxypropylmethyl cellulose, hydroxyethyl cellulose, hydroxyethylmethyl cellulose, hydroxypropyl cellulose, hydroxypropylethyl cellulose, hydroxyethylethyl cellulose, ethyl cellulose and carboxymethyl cellulose; cellulose esters such as cellulose acetate phthalate; and mixed derivatives of ether and/or ester such as phthalyl ester of hydroxypropylmethyl cellulose and acetylsuccinoyl ester of hydroxypropylmethyl cellulose.

The cellulose ether derivative may be preferably cellulose ether, particularly preferably hydroxypropylmethyl cellulose.

Depolymerization is required to reduce the viscosity at 20° C. in a 2% by weight aqueous solution of a cellulose derivative by at least 10%, preferably from 10.0 to 99.7%, more preferably from 10 to 30%. When the reduction is less than 10%, undissolved portions cannot be reduced sufficiently and an advantage or effect of depolymerization is not brought fully.

The cellulose derivative having a viscosity at 20° C. in a 2% by weight aqueous solution of the cellulose derivative of 50 mPa·s or greater, preferably from 50 to 100,000 mPa·s, more preferably from 100 to 30,000 mPa·s, particularly preferably from 1,000 to 30,000 mPa·s, may be preferably subjected to depolymerization. The cellulose derivative having a viscosity at 20° C. of less than 50 mPa·s in a 2% by weight aqueous solution thereof may not be suited because the advantage or effect of the depolymerization does not appear sufficiently. The cellulose derivative having a viscosity at 20° C. of more than 100,000 mPa·s in a 2% by weight aqueous solution thereof is mostly one derived from the high crystalline state of cellulose and effects many undissolved portions. Reduction of these undissolved portions in accordance with the present invention requires long and severe depolymerization work so that it may be uneconomical from the viewpoint of industrial productivity.

The cellulose derivative to be provided for depolymerization can be prepared in accordance with a method as described, for example, in Japanese Patent Application Unexamined Publication No. 8-146501/1996. Either wood pulp or linter pulp can be used as the starting pulp. Esterification may be conducted in accordance with a method as described, for example in Japanese Patent Application Unexamined Publication No. 5-339301/1993, but not particularly limited thereto.

In the preparation of such a cellulose derivative, there is a case where an ester group or an ester group or the like is introduced into fibrous cellulose, by-product chemicals generated in consequence of the introduction are washed away, and the remainder is dried and pulverized. No particular limitation is imposed on the depolymerization of the present invention so that the cellulose derivative either before or after the pulverization may be depolymerized.

The cellulose derivative prior to pulverization having a preferable weight average particle size of 100 to 500 μm as measured using a sieving method may be depolymerized preferably by an acid or an alkali. Although the depolymerization does not progress smoothly when the particle size is unduly large, the depolymerization prior to the pulverization weakens the binding strength by the entanglement of molecules of the cellulose derivative. Accordingly, the subsequent pulverization is facilitated and the heat generated during the pulverization is reduced. As a result, the cellulose derivative is protected from being colored by deterioration or from becoming water-insoluble so that the depolymerization prior to the pulverization is preferable in view of an advantage or effect of the present invention.

On the other hand, when the cellulose derivative is depolymerized after the pulverization, the weight average particle size of the cellulose derivative attained by the pulverization may be preferably 100 μm or less as measured using a sieving method. The cellulose derivative in such powdery form may be preferable because it does not retard the dissolving speed in water and brings a sufficient advantage or effect of the present invention. The pulverization may be done using an impact pulverizer in which the pulverization is effected by collision between materials to be pulverized or collision between the materials and a collision medium, or a ball mill or a roller mill in which the pulverization is effected by catching a material to be pulverized between media. Any grinding manner can be employed.

The viscosity control during the depolymerization can be done by change of the reaction rate or reaction time, caused by the reaction temperature, or an amount of acid, alkali or enzyme to be added. It may be common practice to change the concentration of the acid, alkali or enzyme to be added them because of ease of the control and reduction of the reaction time.

As for the acid, no limitation is imposed on the form of the acid. Whether it is a gas or a liquid, a state of a acid solution or a type of the acid has no effect insofar as the acid provides proton to an aqueous solution of the cellulose derivative. A hydrogen chloride gas, an aqueous solution or an alcohol solution thereof can be typically employed.

As for the amount of the acid, for example, hydrogen chloride may be preferably used in the range of 0.04 to 1% by weight based on the weight of the raw material cellulose derivative. When the amount is less than 0.04% by weight, the reaction rate may be low, resulting in a longer reaction time. When the amount is more than 1% by weight, the reaction control may become difficult and not only it may take time to remove the catalyst but also a large amount of the catalyst may remain in the product as an impurity.

When the acid is used, it may be preferable to have the reaction temperature of 40 to 85° C. and the reaction time of 1 to 2 hours in order to control the reaction rate appropriately.

As for the alkali, any alkali capable of causing alkali hydrolysis in the presence of the alkali and oxygen can be used. Examples may include NaOH and KOH. The NaOH may be preferable because of high hydrolytic ability. In the hydrolysis with an alkali, similar to the hydrolysis with an acid, an alkali solution is used preferably in an amount of from 5 to 50% by weight based on the amount of the raw material cellulose derivative. When the amount is less than 5% by weight, the reaction rate may be low, resulting in a longer reaction time. When the amount is more than 50% by weight, the reaction control may become difficult and not only it may take time to remove the alkali but also a large amount of the alkali may remain in the product as an impurity.

When the alkali is used, it may be preferable to have the reaction temperature of 40 to 85° C. and the reaction time of 1 to 2 hours in order to control the reaction rate appropriately.

As for the enzyme, any cellulolytic enzyme can be used. For example, cellulase can be used. In the hydrolysis with an enzyme, the enzyme may be used preferably in an amount of from 0.01 to 1.0% by weight based on the amount of the raw material cellulose derivative. When the amount is less than 0.01% by weight, the reaction rate is low, resulting in a longer reaction time. When the amount is more than 1.0% by weight, the reaction control may become difficult and not only it may take time for the removal of the enzyme but also a large amount of the enzyme may remain in the product as an impurity.

When the enzyme is used, it may be preferable to have the reaction temperature of 20 to 40° C. The activity of the enzyme may lower when the reaction temperature is outside the above range.

In the hydrolysis with an acid, the acid may be preferably removed by deaeration after the reaction. When the acid remains even after the deaeration, a weak alkali powder such as sodium bicarbonate may be added for neutralization.

Similarly, after hydrolysis with an alkali, neutralization may be conducted by adding preferably a weak acid powder such as oxalic acid.

In the hydrolysis with an enzyme, a cellulose derivative having a desired particle size can be obtained by dispersing or dissolving a cellulose derivative in water, adding from 1 to 10 ppm of an enzyme thereto, and then deactivating the enzyme by heating or adding an alkali or acid thereto, neutralizing, optionally drying and pulverizing.

The number of undissolved portions of the cellulose derivative can be determined, for example, by dissolving at 25° C. the cellulose derivative which has been neutralized after depolymerization, in an aqueous electrolyte solution for measurement ("ISOTON II", product of Beckman Coulter Company) so as to have its concentration of 0.2% by weight and counting the number of undissolved portions existing in 2 ml of the resulting solution using a Coulter counter of Beckman Coulter Company. More specifically, the undissolved portions existing in 2 ml of the resulting solution are regarded as spherical particles and the number of the spherical particles having particle sizes of from 7 to 200 μm is counted. The number of the particles is preferably reduced by at least 10%, preferably from 13 to 90%, more preferably from 20 to 80% by the depolymerization. After depolymerization, it is preferable that the number of the undissolved portions, that is, the number of particles of the cellulose derivative existing in 2 ml of the solution having the above concentration is from 10 to 3,000 particles/2 ml, preferably from 10 to 2,600 particles/2 ml, more preferably from 10 to 1,000 particles/2 ml.

The fundamental embodiments of the present invention will be described by Examples and Comparative Examples. However, it should not be construed that the present invention is limited to or by them.

Examples 1 to 4

Comparative Examples 1 to 4

In a 20-liter Henschel mixer was charged 1 kg of a raw material powder of each cellulose ether shown in Table 1 and having an average particle size of 50 μm as measured using a sieving method. An aqueous solution of hydrogen chloride was sprayed thereto while mixing at 200 rpm. A 50 g portion of the resulting powder was transferred into a 500-ml glass reactor and subjected to reaction while rotating the reactor in a constant temperature water bath. The reaction mixture was placed under a reduced pressure of 60 mmHg or less for 60 minutes to evaporate hydrogen chloride and water. Sodium bicarbonate was added thereto in an amount equivalent to a ½ mole of the hydrogen chloride which had been added, and the resulting mixture was mixed sufficiently for neutralization.

The viscosity at 20° C. in a 2% by weight aqueous solution of the resulting cellulose ether was measured.

The viscosity thus measured, the concentration and amount of hydrogen chloride, the reaction temperature and time in the above reaction are shown in Table 1.

In Comparative Example 1, the viscosity of cellulose ether was controlled to the value shown in Table 1 by adjusting the polymerization degree of raw material pulp without depolymerization of cellulose ether. In Comparative Example 2, the viscosity of cellulose ether was controlled to the value shown in Table 1 by selecting the aging condition of the alkali cellulose without depolymerization of cellulose ether. In Comparative Examples 3 and 4, the viscosity reduction by depolymerization was less than 10%.

aqueous electrolyte solution used exclusively for a Coulter counter so as to have a concentration of 0.2% by weight. Under the same condition as that employed in Example 1, the number of undissolved portions was counted. As a result, it was 900 particles/2 ml.

INDUSTRIAL APPLICABILITY

According to the present invention, a cellulose derivative bringing a reduced number of undissolved portions which are troublesome in its practical use, can be obtained.

The invention claimed is:

1. A depolymerization method for preparing a depolymerized cellulose derivative having a viscosity at 20° C. in a 2%

TABLE 1

| | cellulose ether (before depolymerization) | | | | depolymerization condition | | | | cellulose ether (after depolymerization) | |
| --- | --- | --- | --- | --- | --- | --- | --- | --- | --- | --- |
| | methoxy group (wt %) | hydroxy propoxyl group (wt %) | viscosity *1 (mPa · s) | the number of undissolved particles *2 (particles/2 ml) | concentration of an aqueous solution of hydrogen chloride (wt %) | added amount of hydrogen chloride *3 (wt %) | reaction temp. (° C.) | reaction time (minutes) | viscosity *1 (mPa · s) | the number of undissolved particles *2 (particles/2 ml) |
| Example 1 | 23.0 | 6.5 | 30,000 | 4,500 | 12 | 0.12 | 60 | 60 | 10,000 | 900 |
| Example 2 | 29.3 | 8.6 | 7,100 | 2,800 | 12 | 0.048 | 65 | 90 | 5,200 | 300 |
| Example 3 | 28.8 | 8.9 | 1,000 | 2,000 | 12 | 0.096 | 65 | 90 | 400 | 700 |
| Example 4 | 29.8 | — | 100 | 3,000 | 12 | 0.096 | 65 | 90 | 15 | 2,600 |
| Comp. Ex. 1 | 29.8 | — | 400 | 3,000 | — | — | — | — | — | — |
| Comp. Ex. 2 | 29.8 | — | 400 | 3,200 | — | — | — | — | — | — |
| Comp. Ex. 3 | 29.3 | 8.6 | 7,100 | 4,400 | 1.2 | 0.017 | 65 | 180 | 6,500 | 4,350 |
| Comp. Ex. 4 | 29.8 | — | 1,200 | 2,700 | 1.2 | 0.096 | 65 | 80 | 1,110 | 2,600 |

*1 viscosity at 20° C. in a 2 wt % aqueous solution.
*2 the number of undissolved particles having particle sizes of 7 to 200 μm in a 0.2 wt % aqueous exclusive solution prepared at 25° C.
*3 percent by weight based on the weight of cellulose ether.

Example 5

To 1 part by weight of cellulose ether (viscosity at 20° C. in a 2% by weight aqueous solution: 30000 mPa·s) was added 0.1 part by weight of a 35% by weight aqueous NaOH solution instead of the aqueous solution of hydrogen chloride of Example 1. Alkali hydrolysis reaction took place at 60° C. for 60 minutes as in Example 1. The reaction product was placed under reduced pressure not greater than 60 mmHg at 65° C. for 60 minutes to evaporate water. Oxalic acid was then added thereto in an amount equivalent to that of the above-described NaOH for neutralization. The viscosity at 20° C. in a 2% by weight aqueous solution of the resulting cellulose ether was 100 mPa·s. The number of undissolved portions as measured using a Coulter counter under the same condition as those employed in Example 1 was 4,500 particles/2 ml for the cellulose ether prior to alkali hydrolysis, and 1,000 particles/2 ml for the cellulose ether after alkali hydrolysis and neutralization.

Example 6

To a 2% by weight aqueous solution of cellulose ether used as a starting material in Example 1 was added at 25° C. 0.0001 g of Cellulose AP (produced by Amano Seiyakusha Co., Ltd.) which is a cellulolytic enzyme. The resulting mixture was stirred for 30 minutes to control the viscosity to 1000 mPa·s. The 0.001 g of NaOH was added thereto to deactivate the cellulose AP. Then, 0.001 g of oxalic acid was added thereto for neutralization. The resulting solution was added to an by weight aqueous solution that is reduced by 10% to 30% compared with the viscosity of a water soluble cellulose derivative before the depolymerization so that a number of undissolved floating portions of the depolymerized cellulose derivative in an aqueous solution is decreased compared with a number of undissolved floating portions of the water soluble cellulose derivative before the depolymerization in an aqueous solution, the method of depolymerization comprising the steps of:

a) providing a water soluble cellulose derivative which has a viscosity at 20° C. of 50 mPa·s or greater in a 2% by weight aqueous solution;

b) contacting the water soluble cellulose derivative of step a) with an aqueous solution, an alcohol solution or a gas of hydrogen chloride at a temperature of 40° C. to 85° C. for one to two hours wherein an amount of the hydrogen chloride is from 0.04% to 1% by weight based on the weight of the water soluble cellulose derivative.

2. The method according to claim 1, wherein the water soluble cellulose derivative is a cellulose ether.

3. The method according to claim 1, wherein said water soluble cellulose derivative is hydroxypropylmethyl cellulose.

4. The method according to claim 1, wherein the water soluble cellulose derivative is selected from the group consisting of methyl cellulose, hydroxypropylmethyl cellulose, hydroxyethyl cellulose, hydroxyethylmethyl cellulose, hydroxypropyl cellulose, hydroxypropylethyl cellulose and hydroxyethylethyl cellulose.

* * * * *